United States Patent [19]
Lin et al.

[11] Patent Number: 6,001,818
[45] Date of Patent: Dec. 14, 1999

[54] USE OF 2',3'-DIDEOXYCYTIDIN-2'-ENE (2'-, 3'-DIDEOXY-2'3'-DIDEHYDROCYTIDINE) IN TREATING PATIENTS INFECTED WITH RETROVIRUSES

[75] Inventors: Tai-Shun Lin, North Haven; William H. Prusoff, North Brandford, both of Conn.

[73] Assignee: Yale University, New Haven, Conn.

[21] Appl. No.: 07/727,331

[22] Filed: Jul. 3, 1991

Related U.S. Application Data

[63] Continuation of application No. 07/590,031, Sep. 28, 1990, abandoned, which is a continuation of application No. 06/911,200, Sep. 24, 1986, abandoned.

[51] Int. Cl.⁶ ............................ A61K 31/70; C07H 19/06
[52] U.S. Cl. ............................................. 514/49; 536/28.5
[58] Field of Search ........................ 514/49, 50; 536/28.5

[56] References Cited

U.S. PATENT DOCUMENTS

| | | | |
|---|---|---|---|
| 3,817,982 | 6/1974 | Verheyden et al. | 536/24 |
| 4,710,492 | 12/1987 | Lin et al. | 536/23 |

FOREIGN PATENT DOCUMENTS

| | | | |
|---|---|---|---|
| 0027783 | 3/1977 | Japan | 514/50 |
| 254552 | 10/1986 | Japan. | |
| 8700089 | 8/1988 | Netherlands | A61K 31/70 |

OTHER PUBLICATIONS

Schaeffer et al, Nature, 272, 583–585 (1978).
De Clercq et al, Biochemical Pharmacology 29 1849–1851 (1980).
Broder, "AIDS, Modern Concepts and Therapeutic Challenges", Marcel Dekker, Inc. (1987).
Mitsuya et al, Nature, 325, Feb. 26, 1987, pp. 773–777.
Balzarini et al, Molecular Pharmacology 32 162–167 (1987).
Robins, "Synthetic Antiviral Agents", C & En, Jan. 27, 1986.
Yarchoan et al, the Lancet, Jan. 16, 1988, pp. 76–80.
Fischl et al, The New England Journal of Medicine 317 No. 4 pp. 185–191 (1987).
Schaeffer et al, Nature 272 Apr. 13, 1978 pp. 583–585.
Mitsuya et al, Nature 325 Feb. 26, 1987, pp. 773–778.
Brodel, "AIDS, Modern Concepts and Therapeutic Challenges", Marcel Dekker, Inc. (1987).
De Clercq et al, Biochem. Pharma. 29 pp. 1849–1851 (1980).
Mitsuya et al, Proc. Natl. Aca. Sci USA 82, pp. 7096–7100 (1985).
Derwent Abstract No. 88–170966/25.
J. P. Horwitz, J. Chua, M. Noel, J. T. Donatti, *J. Org. Chem.*, 32, 817 (1967).
H. Mitsuya and S. Broder, *Proc. Natl. Acad. Sci. USA*, 83, 1911–1915, Mar. 1986.
Effects of 2', 3'-Dideoxynucleosides on Mammalian Cells and Viruses pp. 402–408 (1984 M. Anwar Waqar et al).
Inibition of the in vitro infectivity andcytopathic effect of human T–lymphotrophic virus type III/lymphadenopathy–associated virus (HTLV–III/LAV) by 2', 3'–dideoxynucleosides; Hiroaki Mutsuya and Samuel Broder vol. 83 pp. 1911–1915 Mar. 1986 Medical Sciences, *Proc. Natl. Acad. Sci. USA*.
The Anti–HTLV–III (Anti–HIV) and Cytotoxic Activity of 2', 3'–Didehydro–2', 3'–dideoxyribonucleosides: A Comparison with their Parental 2', 3'–Dideoxyribonucleosides Jan Balzarini et al; Mol. Pharmacol. 32(1) Jul. 1987 pp. 162–167.
Inhibition by 2', 3'–Dideoxythymidine of Retroviral infection of Mouse and Human Cells Philip Furmanski et al; Cancer Letters, 8 (1980) pp. 307–315.
Antiviral Activity of 2', 3'–Dideoxycytidin–2'–Ene (2', 3'–Dideoxy–2', 3'–Didehydrocytidine Against Human immunodeficiency Virus in Vitro Tai–Shun Lin et al Biochemical Pharmacology vol. 36 No. 3 pp. 311–316 1987.
Potent andSelective Anti–HTLV–III/LAV activity of 2', 3'–Dideoxycytidinene, the 2', 3'–Unsaturated Derivative of 2', 3'–Dideoxyctyidinee Jan Balzarine et al Biochem Biophys Res. Commun. vol 140 No. 2 1986 pp. 735–742.
Synthesis and Antitumor Activity of Cytosine and Adenine Nucleosides of unsaturated 5–(Aminoacyl)Aminopentofuranoses Carbohydrate Research 78 (1980) Takeshi Adachi et al pp. 67–77.
Lin et al, J. Med. Chem., 26 1691–1696 (1983).

*Primary Examiner*—Gary L. Kunz
*Attorney, Agent, or Firm*—Sprung Kramer Schaefer & Briscoe

[57] ABSTRACT

This invention relates to the use of 2',3'-dideoxycytidin-2'-ene (2',3'-dideoxy-2',3'-didehydrocytidine) in treating patients infected with a retrovirus.

7 Claims, No Drawings

USE OF 2',3'-DIDEOXYCYTIDIN-2'-ENE (2'-,3'-DIDEOXY-2'3'-DIDEHYDROCYTIDINE) IN TREATING PATIENTS INFECTED WITH RETROVIRUSES

This application is a continuation of application Ser. No. 590,031, filed Sep. 28, 1990, now abandoned, which is a continuation of application Ser. No. 911,200, filed Sep. 24, 1986 now abandoned.

GOVERNMENT RIGHTS

This invention was made with United States government support under Grant CA-28852 from the NIH. The United States Government has certain rights in this invention.

BACKGROUND OF THE INVENTION

1. Field of the Invention

The present invention concerns the use of nucleoside 2',3'-dideoxycytidin-2'-ene (2',3'-dideoxy-2',3'-didehydrocytidine) in treating patients infected with retroviruses, especially AIDS.

2. Background Information

The etiological agent of acquired immunodeficiency syndrome ("AIDS") is a retrovirus called lymphadenopathy-associated virus (LAV) (F. Barre-Sinoussi, J. C. Chermann, F. Rey, M. T. Nugeyre, S. Chamaret, J. Gruest, C. Dauguet, C. Axler-Blin, F. Vezinet-Brun, C. Rouzioux, W. Rozenbaum and L. Montagnier, *Science*, 220, 868–870 (1983)) or human T lymphotropic virus III (HTLV III) (M. Popovic, M. G. Sarngadharan, E. Read and R. C. Gallo, *Science*, 224, 497–508 (1984)). Presently, the best evidence supports the concept that these are either the same virus or closely related variants (L. Ratner, W. Haseltine, R. Patarca et al, *Nature*, 313, 227–285 (1985).

2'3'-Dideoxycytidin-2'-ene was first synthesized by Horowitz et al. (J. P. Horwitz, J. Chua, M. Noel, J. T. Donatti, *J. Org. Chem.*, 32, 817 (1967)).

Hiroaki Mitsuya and Samuel Broder, *Proc. Natl. Acad. Sci. USA*, 83, 1911–1915, March 1986, described the testing of purine and pyrimidine nucleoside derivatives, namely, 2',3'-dideoxynucleosides to attempt to inhibit the infectivity and cytopathic effect of human T-lymphotropic virus type III (HTLV-III/LAV) in vitro.

SUMMARY OF THE INVENTION

The present invention is directed to the treatment of warm blooded animals, including humans, infected with a retrovirus, comprising administering to a warm blood animal, e.g., a human patient, an anti-retroviral effective amount of 2',3'-dideoxycytidin-2'-ene (2',3'-dideoxy-2',3'-didehydrocytidine) and pharmaceutically acceptable salts thereof, either alone or in admixture with a diluent or in the form of a medicament.

DETAILED DESCRIPTION OF THE INVENTION

The structure of 2',3'-dideoxycytidin-2'-ene (2',3'-dideoxy-2',3'-didehydrocytidine) is as follows:

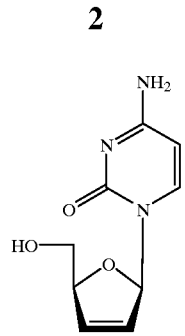

2',3'-dideoxycytidin-2'-ene (2',3'-dideoxy-2',3'-didehydrocytidine) can be prepared according to the following reaction scheme:

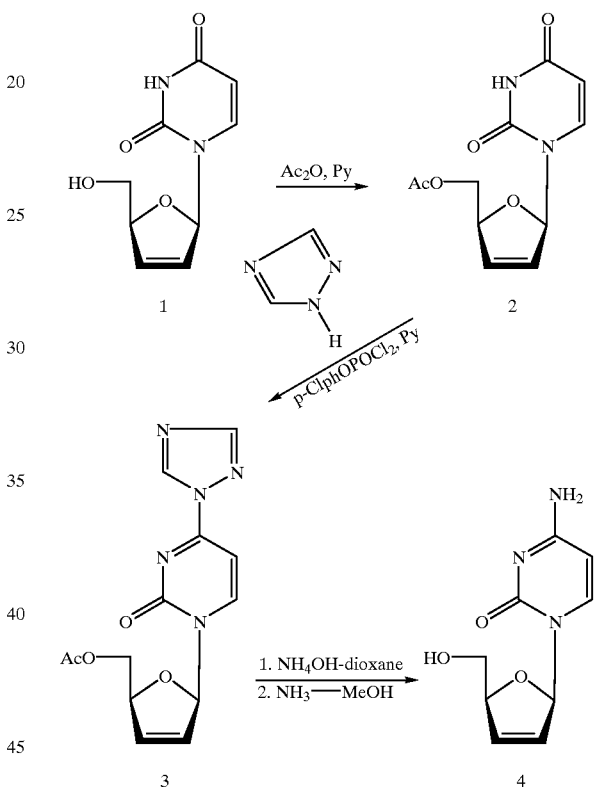

In the above scheme, the following steps are conducted:
Compound 1(2',3'-dideoxyuridin-2'-ene) is acetylated with acetic anhydride ($Ac_2O$) in pyridine (Py), however, can be carried out with actylchloride in a solvent having triethylamine present, to yield the corresponding acetate 5'-acetyl-2',3'-dideoxyuridine-2'-ene which is then treated with 4-chlorophenyl phosphorodichloridate and 1,2,4,-triazole in pyridine at room temperature to yield the 4-triazolylpyrimidinone derivative 3. Subsequent treatment of the 4-triazolylpyrimidinone derivative with aqueous ammonia in dioxane (1:3) is conducted for several hours to several days and then methanolic ammonia is added overnight at room temperature to yield 2',3'-dideoxycytidin-2'-ene (2',3'-dideoxy-2 ',3'-didehydrocytidine) (compound 4).

Applicants have discovered that 2',3'-dideoxycytidin-2'-ene (2',3'-dideoxy-2',3'-didehydrocytidine) has antiviral activity against retroviruses, e.g., murine leukemia virus and HTLV III/LAV virus (the AIDS virus).

Retroviruses are RNA viruses whose genome contains copies of single-stranded RNA. The virion contains reverse transcriptase. Non-limiting examples of retroviruses include leukemia and sarcoma viruses of animals, foamy viruses of primates and some slow viruses, e.g., visna and maedi of sheep.

2',3'-dideoxycytidin-2'-ene has a much better water solubility than that of 3'-azido-3'-deoxythymidine (AZT). In addition, 2',3'-dideoxycytidin-2'-ene can be readily converted to the corresponding hydrochloride and other salts, which will further enhance its water solubility. Water solubility is a critical factor for drug formulation.

The active compound namely, 2',3'-dideoxycytidin-2'-ene (2',3'-dideoxy-2',3'-dideoxydrocytidine) can be administered as a medicament.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day, respectively.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, drageees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g, quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, e.g., $C_{14}$-alcohol with $C_{16}$-fatty acid) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters, microcrystalline cellulose, aluminium metahydroxide, bentonite, agar-agar and tragacanth or mixtures thereof.

The pharmaceutical compositions can also contain coloring agents and preservatives, as well as perfumes and flavoring additions (e.g., peppermint oil and eucalyptus oil) and sweetening agents (e.g., saccharin and aspartame).

The pharmaceutical compositions generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

The preferred daily dose for administration of the medicaments of the invention is 2.5 to 250 mg of active ingredient in the case of intravenous administration and 25 to 250 mg of active ingredient in the case of oral administration.

It is envisaged that this active compound will be administered perorally, parenterally (for example, intramuscularly, intraperitoneally, subcutaneously or intravenously), rectally or locally, preferably orally or parenterally, especially perlingually or intravenously. Preferred pharmaceutical compositions and medicaments are, therefore, those adapted for administration such as oral or parenteral administration. Administration in the method of the invention is preferably oral or parenteral administration.

In general, it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

The invention will now be described with reference to the following non-limiting examples.

EXAMPLE 1

Synthesis of 2',3'-Dideoxycytidin-2'-ene

Acetic anhydride (1.00 g, 10.0 mmol) was added slowly to a stirred solution of compound 1 (0.42 g, 2.00 mmol) in 10 mL of pyridine at 0° C. (ice-bath). The resultant solution was allowed to stand overnight at 4° C. The solvent and the excess acetic anhydride were removed in vacuo. The remaining residue was dissolved in 50 mL of $CHCl_3$, washed in a separatory funnel with 50 mL-portions of $H_2O$ (3 times), saturated $NaHCO_3$ (2 times), and $H_2O$ again (2 times). The $CHCl_3$ solution was clarified with Norit, dried with anhydrous $MgSO_4$, and filtered. The filtrate was then concentrated to a residue which was used immediately without further purification for the next preparation.

The acetate was dissolved in 10 mL of pyridine. While stirring in a cold-water bath, 4-chlorophenyl phosphorodichloridate (0.74 g 3.00 mmol) was added dropwise, followed by the addition of 1,2,4-triazole (0.41 g, 6.00 mmol). The mixture was stirred at room temperature for 3 days and then concentrated under reduced pressure (approximately 30° C.). The resulting residue was dissolved in 25 mL of $CH_2Cl_2$, washed with 25 mL of $H_2O$ (2 times) and 50% $NaHCO_3$ solution (25 mL). The $CH_2Cl_2$ solution was clarified with Norit, dried ($MgSO_4$) and filtered. The filtrate was evaporated to dryness in vacuo to yield a glassy residue (4-triazolylpyrimidinone derivative), which was dissolved in 25 mL of $NH_4OH$-dioxane (1:3). The mixture was stirred for 5 hours at room temperature in a Wheaton pressure bottle. This solution was then concentrated and the remaining residue was stirred overnight in the pressure bottle at room temperature in 25 mL of saturated methanolic ammonia. The solution was then reduced to a small volume in vacuo and chromatographed on a silica gel column ($CHCl_3$-MeOH, 3:1, $R_f$0.34) to yield 0.17 g (40% based on compound 1) of product: mp 163–165° C.; UV (0.1NHCl) λ max 275 nm (ε 11,340), λ min 237 nm; UV (0.1N NaOH) λ max 267 nm (ε 7,010), λ min 247 nm; NMR (Me$_2$SO-d$_6$) γ 3.56 (m, 2H, 5'-H), 4.75 (m, 1H, 4'-H), 4.95 (br s, 1H, 5'-OH, $D_2O$ exchangeable), 5.68 (d, 1H, 5-H), 5.88 (m, 1H, 3'-H, vinyl), 6.33 (m, 1H, 2'-H, vinyl), 6.89 (m, 1H, 1'-H), 7.12–7.19 (br d, 1H, 4-$NH_2$, $D_2O$ exchangeable), 7.68 (d, 1H, 6-H).

The starting compound 1 was prepared from 2'-deoxyuridine by the methodology of Horwitz et al. (J. P. Horwitz, J. Chua, M. Noel, J. T. Donnatti, *J. Org. Chem.*, 32, 817, (1967)).

EXAMPLE 2

Biological Activity

Assay Procedure For Antiviral Screeining Against Moloney Murine Leukemia Virus (M-MuLV) By XC-Assay:

The XC assay system is an indirect method for quantitation of murine-leukemia virus (MULV) originally described by V. Klement et al, *Proc. Nat'l. Acad Sci.*, 63, 753–758, (1969) and modified by W. Rowe et al, *Virology*, 42, 1136–1139, (1970). This test is based on the development of syncytial changes in the XC cell line when it is co-cultivated with mouse fibroblast cells (SC-1 cells) productively infected with MULV. The XC cell line was derived from a rat tumor induced by the Prague strain of Rous Sarcoma Virus (RSV) (J. Svobada et al, *Folia Biol.*, 9, 77–81, (1983)). This cell line contains the RSV genome, but does not produce infectious virus in the absence of a helper virus. 10E6 SC-1 cells were seeded in Earls' Minimum Essential Medium (EMEM)-10% Fetal Bovine Serum (FBS) onto 60 mm petri dishes. The following day, the cells were inoculated with 0.5 mL of a virus dilution containing 25 μg/mL of DEAE-dextran. The dishes were maintained for one hour at 37° C. in a humidified 5% $CO_2$ incubator. The virus inoculum was then removed and replaced with 5mL of medium containing appropriate concentration of the test compound (two dishes/concentration). A medium containing 10% FBS was added to the virus control dishes. The medium (with or without the test compound) was changed at 48 hours.

Five days after virus inoculation, the culture fluid was decanted and the cells were irradiated with a "GE" germicidal bulb for 30 seconds (60 ergs/mm$^2$/sec UV-light). The cultures were immediately overlaid with $10^6$ XC cells in 0.5 mL of EMEM-10% FBS/dish. The medium was changed at 2 day intervals. Four days after XC cells addition, cultures were simultaneously fixed and stained with Giemsa stain for 10–15 minutes.

Virus plaques (i.e., areas of the cell sheet containing syncytial cells or focal masses of multinucleated giant cells) were counted using an inverted microscope. The percent inhibition in virus plaque number at each drug concentration was calculated as follows:

$$\% \text{ Inhibition} = 100 - \left[ \frac{\text{average \# of syncytia at conc. of test compound}}{\text{average \# of syncytia in the virus control}} \times 100 \right]$$

$ED_{50}$ ($ID_{50}$): Accumulative % Inhibition using Reed-Muench Method $ED_{50}$: Effective Dose to inhibit 50%

The median inhibitory dose ($ID_{50}$) of each compound was calculated from the percent inhibition results using the Reed-Muench Method.

The antiviral activity of 2',3'-dideoxycytidin-2'-ene compared against 2',3'-dideoxycytidine is shown as follows in Table 1. 2',3'-Dideoxycytidine is a known potent compound against HTLV-III/LAV virus in culture (Mitsuya and Broder, supra).

TABLE 1

| Compound | $ID_{50}$ (μM) (Moloney Murine Leukemia Virus) |
| --- | --- |
| 2',3'-dideoxycytidin-2'-ene | 3.7 |
| 2',3'-dideoxycytidine | 4.0 |

EXAMPLE 3

Antiviral Activity of 2'3'-dideoxy-2',3'-didehydrocytidine (2',3'-dideoxycytidin-2'-ene)

A. Cellular Assay of Inhibition of HTLV-III/LAV (cytopathic effect), Fluorescence, Viability)

Nucleoside Analogs: One millimolar solutions were prepared in glass distilled water and filter sterilized through 0.2μ filters. Subsequent dilutions were prepared in RPMI 1640 medium containing 15% fetal calf serum, penicillin, streptomycin and glutamine.

Cell Cultures: The HTLV-1 transformed cell line MT-2 (MT-2 cells are lymphocytes derived from placenta cord blood which were transformed by HTLV-I) were suspended at 0.5×10$^6$ cells/ml in each of the media samples having the drug concentrations outlined in Table 2. Cultures were incubated in the drug overnight (approximately 9 hours) in 24 well TC plates at 0.66 ml/well.

Virus: HTLV-III/LAV prepared in PHA (phytohemagglutinin A) blasts, titering approximately $10^5$ infectious units/ml was added in 10 μl amounts to 0.66 ml cultures. PHA stimulates lymphocytes to proliferate and undergo blast transformation. One thousand infectious center forming units were added to duplicate wells of each drug concentration. A cell control was mock-infected at each drug concentration.

Assay: On day 7 post-infection, day 8 post-drug treatment, the cultures were visually inspected for cytopathic effect and harvested individually by centrifugation at 1200 RPM in a TJ6 centrifuge, using aerosolve cannisters. The cells were resuspended in 200 μl PBS. 20 μl from each duplicate were pooled and stained for viability using the trypan blue exclusion method. 20 μl of each duplicate were spotted onto multiwell slides, dried and acetone-fixed for fluorescent studies.

Fluorescent Assay: Acetone-fixed cells were stained by monoclonal antibody αp18 (monoclonal antibody (αp18 is directed against HTLV III virus), which had been directly conjugated and contained Evans blue counterstain added to the monoclonal diluent. Cell counts reflect one field from each duplicate for each drug concentration.

Conclusion: The data in Table 2 show that 2',3'-dideoxy-2',3'-didehydrocytidine (2',3'-dideoxy-cytidin-2'-ene) has antiviral activity against the HTLV-III/LAV infection in vitro and that the effective dose falls in the same range as 2',3'-dideoxycytidine.

TABLE 2

| Compound | % Fluoresence* | | % Apparent CPE** | | % Viable Cells*** | |
| --- | --- | --- | --- | --- | --- | --- |
| | 0.5 μM | 1.0 μM | 0.5 μM | 1.0 μM | 0.5 μM | 1.0 μM |
| 2',3'-dideoxycytidine | 4.3 ± 0.3 | 0.2 ± 0.1 | 40 ± 10 | 1.0 ± 0.0 | 75 | 96 |
| 2',3'-dideoxy-2',3'-didehydrocytidine (2',3'-dideoxycytidin-2'-ene | 5.6 ± 5.5 | 1.1 ± 0.1 | 90 ± 0.0 | 0.5 ± 0.5 | 22 | 90 |

*% Fluorescence is the number of fluorescent cells divided by the total number of cells scored in the microscope field viewed.
**% Apparent CPE is the number of destroyed cells divided by the total number of cells scored in the microscope field viewed. It relates to visual inspection for cytopathic effect.
***The % Viable Cells is the number of cells that excluded the dye trypan blue divided by the number of cells scored in a given microscope field. This method gives the percent of metabolically living cells.

B. Reverse Transcriptase Assay

The following references describe the reverse transcriptase assay:

A. M. Prince, B. Horowitz, H. Dichtelmueller, W. Stefan and R. C. Gallo, *Cancer Research* [Suppl], 45, 4592S, (1985); T. S. Sarin, Y. Taguchi, S. Daisy, A. Thornton, R. C. Gallo and B. Oberg, *Biochem. Pharmacol.*, 34, 4075, (1985); and Bethesda Research Laboratory Catalog and Reference Guide, p. 17, 1985.

This procedure evaluated the antiviral activity of compounds against the human immunodeficiency virus (HIV or HTLV-III/LAV) in infected mitogen stimulated human peripheral blood mononuclear cells. On day 5 after infection the virus was harvested by centrifugation, and the virus pellet was disrupted and subjected to a reverse transcriptase assay. Results for this assay are given below in Table 3.

TABLE 3

| | % Inhibition | |
| --- | --- | --- |
| Concentration (μM) | 2',3'-dideoxycytidine | 2',3'-dideoxy-2',3'-didehydrocytidine (2',3'-dideoxycytidin-2'-ene) |
| 0.001 μM | 5.7 | 29 |
| 0.01 | 37 | 61 |
| 0.1 | 95 | 66 |
| 1.0 | 93 | 92 |

Conclusion

The data in Table 3 confirm the inhibitory activity of 2',3'-dideoxy-2',3'-didehydrocytidine (2',3'-dideoxycytidin-2'-ene).

It will be appreciated that the instant specification and claims are set forth by way of illustration and not limitation, and that various modifications and changes may be made without departing from the spirit and scope of the present invention.

What is claimed is:

1. A method for treating warm blooded animals infected with a retrovirus, the method comprising administering to the warm blooded animal an anti-retroviral effective amount of 2',3'-dideoxy-2',3'-didehydrocytidine or a pharmaceutically acceptable salt thereof, either alone or in admixture with a diluent or in the form of a medicament.

2. A method according to claim 1, wherein the retrovirus is HTLV III/LAV.

3. A method according to claim 1, wherein the retrovirus is murine leukemia virus.

4. A method according to claim 1, wherein the 2',3'-dideoxy-2',3'-didehydrocytidine is administered intravenously in an amount of 0.01 to 10 mg per kg body weight per day.

5. A method according to claim 1, wherein the 2',3'-dideoxy-2',3'-didehydrocytidine is administered orally in an amount of 0.05 to 20 mg per kg body weight per day.

6. A method for treating human blood cells infected with HIV comprising administering to said cells an antiretroviral amount of 2',3'-dideoxy-2',3'-didehydrocytidine or a pharmaceutically acceptable salt thereof, either alone or in admixture with a diluent or in the form of a medicament.

7. A pharmaceutical composition for the treatment of AIDS and AIDS related diseases, which comprises a therapeutically effective amount of 2',3'-didehydro-2',3'-dideoxycytidine as an active ingredient for inhibiting the replication and the effects of HIV, and at least one pharmaceutically acceptable carrier therefor, wherein the pharmaceutically acceptable carrier comprises at least one of an aqueous solvent, non-aqueous solvent, stabilizer, emulsifier, detergent, additive, dye or aromatizer, said composition being in the form of powders, suspensions, solutions, sprays, emulsions, unguents or creams.

* * * * *